United States Patent [19]
Goodsmith

[11] Patent Number: 4,649,753
[45] Date of Patent: Mar. 17, 1987

[54] VERIFICATION PROBE
[75] Inventor: Dale H. Goodsmith, Brighton, Mich.
[73] Assignee: Multifastener Corporation, Detroit, Mich.
[21] Appl. No.: 849,316
[22] Filed: Apr. 8, 1986
[51] Int. Cl.[4] ............................................. F16B 31/02
[52] U.S. Cl. ..................................... 73/865.8; 73/761
[58] Field of Search ................ 73/760, 761, 805, 806, 73/816, 826, 827, 831, 832, 834, 837, 865.8, 865.9, 866.5

[56] References Cited
U.S. PATENT DOCUMENTS 3,563,087  2/1971  Brunelle et al. ....................... 73/761
3,618,396  11/1971  Julien ................................... 73/865.8
4,475,403  10/1984  Lentz ................................... 73/826
4,554,838  11/1985  Paus ..................................... 73/834

Primary Examiner—Michael J. Tokar
Assistant Examiner—Robert R. Raevis
Attorney, Agent, or Firm—Cullen, Sloman, Cantor, Grauer, Scott & Rutherford

[57] ABSTRACT

The present invention relates to an automatic verification probe for verifying the proper installation of a fastener to a workpiece, in the preferred embodiment, a plurality of probes are used in a single press to test each fastener for proper installation. The probe has a fluid-operated extensible member mounted to the ram or base of the press. By extension of the member, each fastener is tested individually to verify proper location, absence of material in the thread cylinder and minimum retention capability.

9 Claims, 4 Drawing Figures

VERIFICATION PROBE

FIELD OF THE INVENTION

This invention relates to a verification probe having a controlled extensible member particularly suited for verifying the proper installation of fasteners, such as for example pierce or clench nuts.

BACKGROUND OF THE INVENTION

The verification probe of this invention is designed for the nondestructive testing of a fastener to determine if the fastener has been properly installed on a workpiece. Preferably, the fastener is of the type having a thread cylinder which communicates with an axially aligned opening in the workpiece, such as for example, a self-piercing nut as disclosed in U.S. Pat. No. 3,648,747 assigned to the assignee of the instant application. The pierce nut includes a pilot portion which pierces an opening in a panel, a pair of flanges on opposed sides of the pilot having panel-bearing faces and re-entrant grooves in the flangebearing surfaces adjacent the pilot. Upon forced engagement with the panel, the pilot pierces an opening in the panel and the pierced panel edges are deformed into and retained by the re-entrant grooves.

Typically, several fasteners of the above type will be simultaneously pressed into a part as the part is being formed. Each fastener must be properly installed which requires it to be properly positioned on the panel, the slug formed by the fastener to be discharged from the thread cylinder and the fastener to have a minimum retention capability.

There are no devices or processes available that perform all three checks for proper installation in one operation, that is, checking to verify slug removal, proper location and minimum retention. Nor are there any that perform all three checks on every fastener individually.

Applicant is aware of only three methods presently used to test fasteners. The first method involves randomly selecting a part from a batch of parts and striking one or more fasteners with a hammer. The force used to strike the fastener is determined by the person doing the test to be within the desired retention force of the fastener. Obviously, this is a very imprecise method. Further, it doesn't determine the proper location of the part or verify removal of the slug or test every fastener on every part.

In the second test, a part is selected from a batch of parts and a hydraulic cylinder is used to apply force to the fastener until the fastener releases, from the part. If the applied force is within a predetermined range, the batch of parts is considered to be good. If not, further testing may be required and the result may be the rejection of an entire batch of parts. Again, the second method does not test each fastener on each part and does not test for the proper positioning of the fastener on the part. Further, this test is a destructive test requiring the destruction of at least one fastener and, therefore, one part.

The last known method uses fiber-optics and television systems to test for the proper location of the fastener and to verify that the slug has been removed. Of course, this method does not test for retention requiring one of the above tests to be used.

As indicated earlier, in order for a part to be good, every fastener must be properly installed, which requires the fastener to be properly positioned and properly attached. None of the known methods of testing provide for the non-destructive testing of every fastener in one operation.

BRIEF DESCRIPTION OF THE INVENTION

The verification probe of the present invention provides a method and apparatus for non-destructive testing of all installed fasteners. Each probe tests for proper location and proper attachment of an individual fastener without destroying any properly installed fasteners.

Each probe includes a fluid cylinder and an extensible member operatively received within the cylinder. The extensible member has a piston opposite the workpiece and an elongated shaft extending from the piston in the direction of the workpiece. Pressurized fluid is introduced to the cylinder by a control means which regulates the movement of the extensible member with respect to the fastener in relation to the press cycle and position of the piston.

The control means initially introduces fluid to the cylinder, moving the extensible member to a position adjacent the workpiece. If the fastener is offset or absent or if the slug has not been discharged, further movement of the piston is prevented and this condition is indicated. If the fastener is properly positioned and the slug absent, the extensible member engages the thread cylinder of the fastener whereupon the control means introduces increased pressurized fluid to the cylinder.

The increased pressure exerts a predetermined minimum retention force or push-off load upon the fastener urging the fastener to break free of the workpiece. If the fastener breaks free, this condition is indicated; if the fastener is retained upon the workpiece, the fastener is properly installed and the probe receives another part for testing.

The method for verifying the proper attachment of the fastener to a workpiece involves the steps of first introducing pressurized fluid to the fluid cylinder which moves the extensible member to the surface of the workpiece at the intended location of a fastener. If the fastener is absent, offset or if the slug is present, the condition is indicated.

The next step involves introducing further pressurized fluid to the cylinder, moving the extensible member into the thread cylinder of the fasteener and indicating the position. Thereafter, increased pressurized fluid is introduced into the cylinder urging the extensible member to a failure position corresponding to release of the fastener from the workpiece. If the extensible member reaches the failure position, this condition is indicated. If the extensible member does not reach the failure position, the fastener is properly installed and the product is good.

As should be apparent, the present invention provides a nondestructive method and apparatus for testing the installation of each and every fastener on a part.

DETAILED DESCRIPTION OF THE INVENTION

Figure 1:
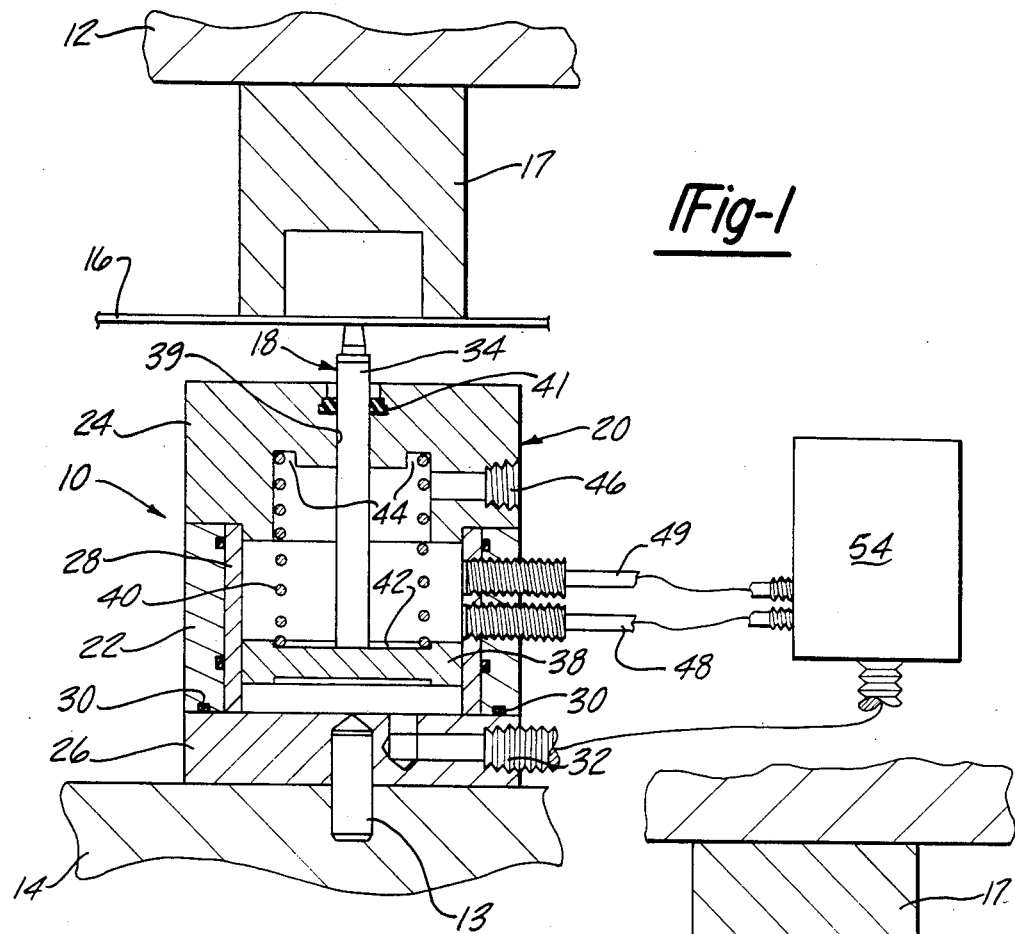
FIG. 1 illustrates a cross-sectional view of the probe of the present invention with an absent fastener.
Figure 2:
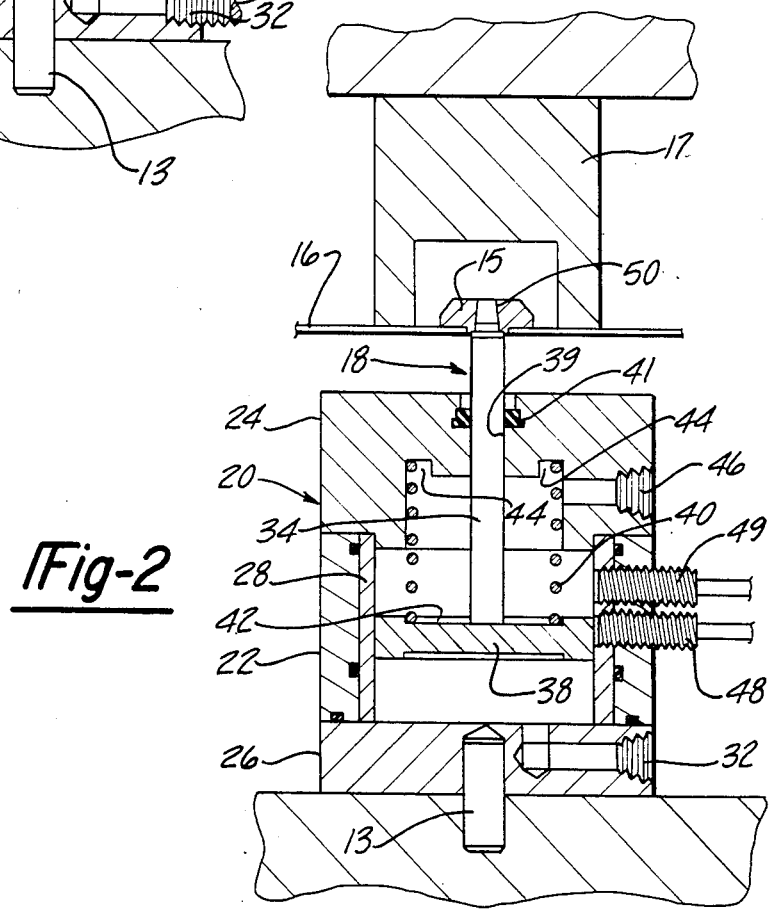
FIG. 2 is a cross-sectional view of the probe engaging the thread cylinder of a fastener properly positioned.
Figure 3:
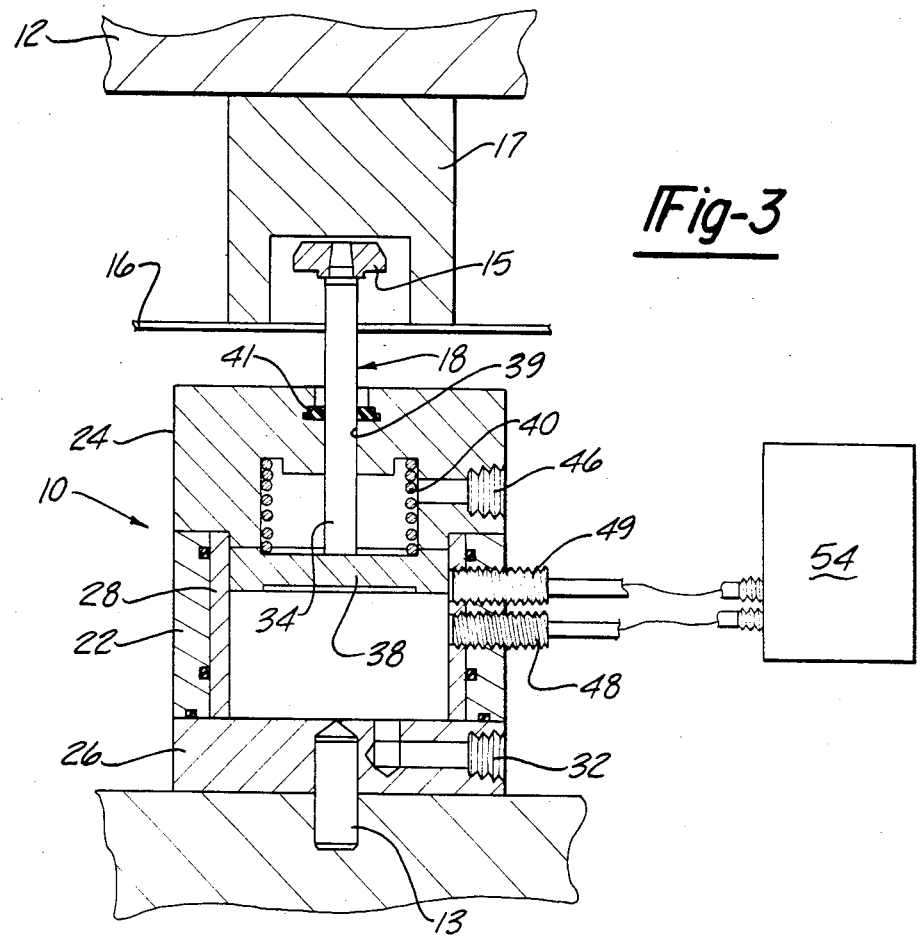
FIG. 3 is a cross-sectional view of the probe with an improperly installed fastener.

With reference to FIGS. 1 through 3, the verification probe of the present invention is shown generally at 10. In the preferred embodiment, a plurality of probes 10 are mounted by a mounting pin 13 between the upper and lower die shoes 12 and 14 of a testing press with one probe for each fastener to be installed. In this manner, every fastener is tested individually. The following description will be limited to a single probe with the understanding that, in the preferred embodiment, there are several probes operating simultaneously to test each fastener on each part.

The testing press forms a testing station in a continuous feed press operation. A primary station continuously forms metal blanks into the desired parts 16 and either simultaneously or at a later station installs fasteners 15. Once the fasteners 15 are installed, part 16 moves to the testing station. Shoes 12 and 14 are closed about the part and probes 10, in conjunction with entrapment blocks 17, verify the proper installation of all fasteners 15. Proper installation requires the proper positioning and alignment of each fastener 15, the removal of slugs from the thread cylinder of the fasteners and at least a minimum retention force in each fastener so they will not release from the part during use.

Probe 10 includes an extensible member 18 reciprocally received within a sleeve cylinder 28 mounted in a fluid cylinder 20. Cylinder 20 includes a cylinder housing 22 surrounding sleeve cylinder 28 and upper and lower plates 24 and 26 respectively. O-rings 30 are provided to ensure that cylinder 20 is air-tight.

Member 18 is extended in the direction of work surface 16 by pressurized fluid that is introduced into cylinder 20 at inlet port 32. Member 18 includes a piston 38 and an elongated shaft 34 that extends through bore 39 and wiper seal 41 in plate 24. A spring means 40 is positioned between upper plate 24 and the top surface of piston 38 to bias piston 38 against the fluid pressure and return it to its initial position. In the preferred embodiment, spring means 40 is received within relieved portions 42 and 44 of piston 38 and upper plate 44 respectively. An exhaust port 46 is provided opposite inlet port 32 to exhaust fluid within sleeve cylinder 28.

The position of piston 38 is determined by sensors 48 and 49 that are threadably received within sleeve cylinder 28. The sensors 48 and 49 detect and communicate the position of piston 38 and, correspondingly, the presence and proper retention of the fastener. In the preferred embodiment, the sensing means are conventional electrical proximity switches; however, conventional air switches are within the intended scope of the invention.

Probe 10 functions directly in relation to the cycle of the press. Typically, a press works in a 360 degree cycle. With reference to FIG. 1, the press is at 180 degrees in its cycle corresponding to the press being closed. At 180 degrees, pressurized fluid is introduced to port 32 and piston 38 is forced in the direction of the work surface 16. A control means 54 regulates this introduction of fluid from signals received from the press and sensors 48 and 49.

As illustrated in FIG. 1, the nut is absent, preventing further movement of extensible member 18. This will also occur if the fastener is misaligned, or has a slug from the work surface in the thread cylinder. As the press continues past 180 degrees in its cycle, piston 38 has not contacted sensing means 48. This condition, in the preferred embodiment, shuts down the press and lights an indicator light. This requires the operator to open the press, remove the defective part and recycle the press before continuing.

With reference to FIG. 2, a fastener 15 is properly positioned. As is apparent, extensible member 18 has moved into thread cylinder 50 of fastener 15 allowing piston 38 to contact sensor 48. As the press continues through 180 degrees, piston 38 is in contact with sensor 48 permitting the press to continue. Also, as the press continues through 180 degrees, control means 54 increases the fluid pressure to cylinder 28.

The increased pressure is a predetermined retention pressure or push-off pressure that is necessary to ensure proper retention of fastener 15. This predetermined pressure is less than the actual push-off pressure of the fastener. As the press cycles between 180 degrees and 360 degrees, the increased pressure urges piston 38 to a failure position as illustrated in FIG. 3. In this position, piston 38 has moved past sensing means 48 and into contact with sensing means 49 which indicates that the fastener has broken loose from the work surface. In the preferred embodiment, the press will automatically shut down and an indicator will light. This condition requires the press operator to open the press, remove the defective part and recycle the press to continue operation. If piston 38 does not reach sensing means 49, the press completes its cycle, opening at 360 degrees to receive another part to be tested.

Figure 4:
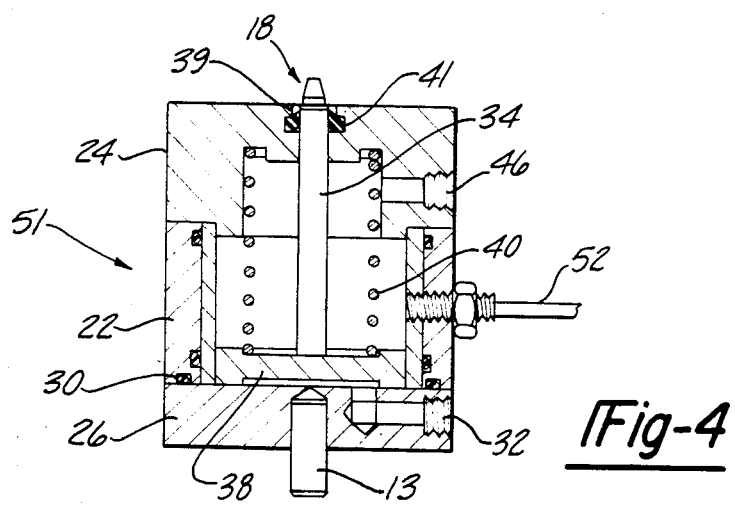
FIG. 4 is a cross-sectional view of a second embodiment of the probe.

With reference to FIG. 4, a further embodiment of the present invention is illustrated at 51. In this embodiment, like parts have identical reference numerals. The difference between the probe illustrated in FIG. 4 and the probe illustrated in FIGS. 1 through 3 is the use of a single conventional sensing means 52 rather than dual sensing means 48 and 49.

Probe 51 operates in the same 360 degree cycle as probe 10. As fluid is introduced to cylinder 28 and the press moves past 180 degrees, piston 38 must contact probe 52 or the press will shut down. If contact is made, the nut is properly positioned and there is no slug in the thread cylinder. As the press continues, control means 54 introduces increased fluid pressure to inlet port 32 urging extensible member 18 to the failure position. If extensible member 18 reaches the failure position, piston 38 moves past probe 52, shutting down the press and lighting an indicator. If extensible member 18 does not reach the failure position, piston 38 continues to contact sensing means 52, permitting the press to complete its cycle and indicating that the fastener has been properly installed. The press then opens, discharges the tested part and receives a new part to be tested.

It will be apparent to those skilled in the art that the foregoing disclosure is explanatory in nature rather than limiting, the invention being limited only by the appended claims.

What is claimed is:

1. An automatic probe for use in a press for verifying the proper installation of a fastener in an opening in a workpiece, the fastener having a thread cylinder axially aligned within the opening in the workpiece, the probe comprising:

an extensible member; and control means operatively associated with the extensible member for regulating the extensible member; the control means actuating the extensible member as the press closes, initially extending the extensible member to a first position to engage the fastener at the thread cylinder, the control means further biasing the extensible member to a second position against the installed fastener under a predetermined load, the load being less than a load necessary to push-off the fastener from the workpiece confirming proper installation of the fastener on the workpiece;

the control means indicating failure when the extensible member fails to travel to the first position or travel past the second position.

2. The automatic probe of claim 1, further comprising a fluid cylinder operatively mounted within the press with the extensible member operatively received within the fluid cylinder;

wherein the control means regulates the extensible member by controlling the fluid introduced to the fluid cylinder.

3. The automatic probe of claim 2, wherein the extensible member includes a piston opposite the workpiece reciprocally received within the fluid cylinder and an elongated shaft extending from the piston in the direction of the workpiece.

4. The automatic probe of claim 1, wherein the control means includes a sensing means in operative contact with the extensible member, the sensing means detecting the position of the extensible member.

5. A method for verifying the proper installation of a fastener in an opening in a workpiece, the fastener having a thread cylinder axially aligned within the opening in the workpiece, the method comprising the steps of:

(1) actuating a fluid cylinder having an extensible member operatively mounted therein;

(2) urging the extensible member to a first position into engagement with the fastener at the thread cylinder;

(3) further urging the extensible member to a second position against the installed fastener under a predetermined load less than a load necessary to push-off the fastener from the workpiece confirming the proper installation of the fastener on the workpiece;

(4) indicating failure when the extensible member travels a distance less than the first position; and (5) indicating failure when the extensible member travels a distance greater than the second position.

6. The method of claim 5, further comprising the steps of:

(6) providing a plurality of fluid cylinders having extensible members for testing a plurality of fasteners; and (7) simultaneously performing steps (1)–(5) on each fastener in the workpiece.

7. An automatic probe for use in a reciprocal press having upper and lower plattens for verifying the proper installation of a fastener in an opening in a workpiece, said fastener having a thread cylinder axially aligned within the opening in said workpiece, said automatic probe comprising:

a fluid cylinder operatively mounted with respect to one of said plattens;

an entrapment block mounted in said opposite platten directly opposite said cylinder;

an extensible member received within said fluid cylinder extensible in the direction of said entrapment block;

sensing means mounted within said fluid cylinder for signaling the position of said extensible member with respect to said entrapment block;

control means for regulating the amount of fluid supplied to said fluid cylinder and the operation of said press, said control means receiving signals from said sensing means and said press;

said control means initially introducing fluid to said fluid cylinder as said press closes moving said extensible member to a position contiguous with said workpiece; if said fastener is offset or absent, further movement of said extensible member is prevented with said control means so indicating by shutting down said press; if said fastener is properly positioned, said extensible member engages said thread cylinder whereupon said control means introduces further fluid to said fluid cylinder in response to signals received from said sensing means and said press;

said further fluid exerting a predetermined retention force upon said fastener urging said extensible member to a position corresponding to failure of said fastener with said control means so indicating by shutting down said press; and if said member fails to reach said further position, said fastener is properly attached to said workpiece permitting said press to open and receive another part for testing.

8. The automatic probe of claim 7, wherein a plurality of fluid cylinders and entrapment blocks are mounted within said press, said plurality corresponding to the number of installed fasteners;

whereby every fastener on each workpiece is simultaneously tested to verify proper installation.

9. The automatic probe of claim 7, further comprising spring means to bias said extensible member away from said entrapment block.

* * * * *